United States Patent
Andre (10) Patent No.: US 9,488,577 B2
(45) Date of Patent: Nov. 8, 2016

(54) MINIATURE GAS SENSOR

(71) Applicant: Commissariat à l'énergie atomique et aux énergies alternatives, Paris (FR)

(72) Inventor: Luc Andre, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/589,340

(22) Filed: Jan. 5, 2015

(65) Prior Publication Data

US 2015/0192517 A1    Jul. 9, 2015

(30) Foreign Application Priority Data

Jan. 6, 2014   (FR) ...................................... 14 50048

(51) Int. Cl.
   *G01N 21/61* (2006.01)
   *G01N 21/3504* (2014.01)
   *G01N 21/03* (2006.01)

(52) U.S. Cl.
   CPC ............ *G01N 21/61* (2013.01); *G01N 21/031* (2013.01); *G01N 21/3504* (2013.01); *G01N 2201/0636* (2013.01); *G01N 2201/0638* (2013.01)

(58) Field of Classification Search
   CPC ............. G01N 21/61; G01N 21/3504; G01N 2201/0636
   See application file for complete search history.

(56) References Cited

U.S. PATENT DOCUMENTS

| | | | | |
|---|---|---|---|---|
| 4,394,575 A | * | 7/1983 | Nelson | G01J 5/602 250/343 |
| 4,933,545 A | * | 6/1990 | Saaski | G01L 9/0079 250/227.14 |
| 5,459,566 A | | 10/1995 | Pearson | |
| 5,468,961 A | | 11/1995 | Gradon | |
| 5,550,375 A | | 8/1996 | Peters et al. | |
| 2003/0136911 A1 | | 7/2003 | Martin | |
| 2009/0200466 A1 | * | 8/2009 | Mammen | G06T 5/50 250/330 |

FOREIGN PATENT DOCUMENTS

FR        2 390 725 A1   12/1978
WO     2011/151629 A1   12/2011

OTHER PUBLICATIONS

Search Report issued in French Patent Application No. 14 50048 dated Oct. 31, 2014.
Antonella Amoruso et al., "Long-base-line multiple reflection cell for UV and visible spectroscopy" Review of Scientific Instruments, vol. 66, No. 10, Oct. 1, 1995.

* cited by examiner

*Primary Examiner* — David Porta
*Assistant Examiner* — Faye Boosalis
(74) *Attorney, Agent, or Firm* — Pearne & Gordon LLP (57) ABSTRACT

A gas sensor (20) comprising a substrate (231); an objective (211) situated on the substrate (231), adapted to collect a light beam (212, 213) emitted by a light source (210); an eyepiece (250) situated on the substrate (231), adapted to collect an incident light beam to focus it on a detector (251); return reflective surfaces (281, 282), situated facing said substrate; and at least one field lens (221), arranged on an intermediate reflective surface (222) formed on the substrate (231), and adapted to deviate the rays (213) of the light beam emitted by the light source, to bring them closer to the optical axis of the eyepiece (250).

15 Claims, 6 Drawing Sheets

MINIATURE GAS SENSOR

TECHNICAL FIELD

The present invention relates to the field of gas sensors, in particular the field of gas sensors implementing the absorption of an infrared radiation.

STATE OF THE PRIOR ART

Gas sensors implementing the technique known as NDIR, for "Non Dispersive Infra Red" are known in the prior art. According to this technique, a light beam is emitted in the infrared (wavelength comprised between 1 µm and 10 µm), inside a cavity receiving a gas to be detected. The light beam is partially absorbed by said gas. The absorption wavelength depends on the nature of the gas. A light source emitting a light beam at the absorption wavelength of the gas to be detected is generally used. Alternatively, a wavelength filter is used intended to eliminate spectral contributions not belonging to a spectral band of interest centred on the absorption wavelength. A detector makes it possible to measure the light intensity at the absorption wavelength, after partial absorption by said gas. It is thus possible to detect the presence of a determined gas, and even its concentration in the cavity using Beer-Lambert's law. It will be recalled that for a predetermined gas and having an absorption wavelength, Beer-Lambert's law links:
  the light intensity at the absorption wavelength before partial absorption by said gas ($I_0$);
  the light intensity at the absorption wavelength after partial absorption by said gas (I);
  the length of the optical path travelled in the gaseous medium ($l_g$);
  the concentration of gas in the medium (C); and
  the molar absorptivity of said gas ($\in$):

$$I = I_0 * e^{-\in l_g C}$$

In these known gas sensors, the light source may be a light emitting diode, emitting a beam centred on the desired absorption wavelength. A filament acting as a black body can also be used. In this case, advantageously a filter as defined above, as well as a collimation optic, are used.

Figure 1:
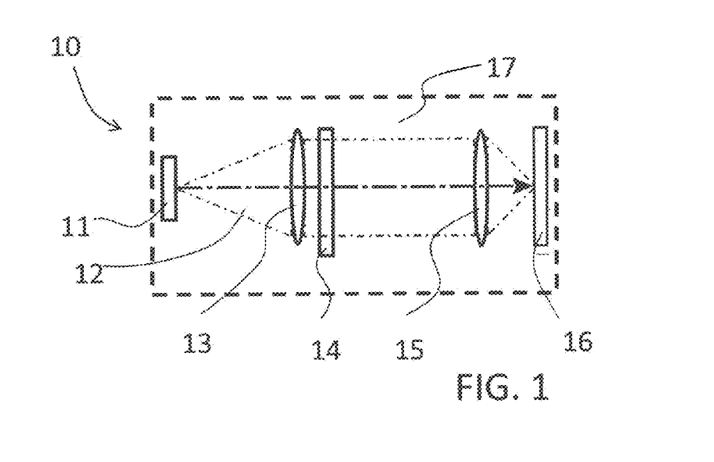
FIG. 1 schematically illustrates a gas sensor according to the prior art.

In FIG. 1 is represented an example of gas sensor 10 according to the prior art. The light source 11 is formed of a filament, and emits a light beam 12 in the direction of a collimation optic 13. A filter 14 eliminates the spectral contributions of the light beam 12 lying outside of a useful spectral band associated with the gas to be detected. Near to the detector 16 is located a focusing optic 15, adapted to focus the light beam on said detector. The detector 16 makes it possible to express, in an electric signal, the light intensity of the incident light beam. The whole thing is situated inside a cavity 17 receiving said gas to be detected.

For a given gas, a minimum length of the optical path covered by the light beam in the cavity may be defined, making it possible to obtain a sufficiently precise measurement of the gas concentration.

Different solutions for producing a miniaturised gas sensor are known in the prior art.

For example, the patent document US 2003/0136911 proposes using a cavity in which the walls are formed of two parallel flat surfaces connected by a lateral surface orthogonal to the two parallel flat surfaces. The parallel flat surfaces have a truncated ellipse shape. Two straight lines go from the truncated ends of the ellipse and converge towards the detector. The light source is placed in a first focus of the ellipse, whereas the detector is placed at the second focus of the ellipse. The light rays emitted by the light source are reflected at least once on the lateral surface of the cavity, before reaching the detector. They thus cover an optical path greater than the distance separating the light source and the detector.

A drawback of such a cavity is that it has to be aligned very precisely relative to the light source and to the detector. Moreover, it offers relatively restricted possibilities of miniaturisation because most of the light rays only make a single reflection on the lateral surface before reaching the detector.

An objective of the present invention is to propose a gas sensor having a higher compactness than gas sensors of the prior art, for a same length of optical path travelled by a light beam inside the cavity receiving the gas to be studied.

DESCRIPTION OF THE INVENTION

This objective is attained with a gas sensor comprising a cavity for receiving a gas, a light source and a detector.

The gas sensor according to the invention comprises:
  a substrate;
  an objective situated on the substrate, adapted to collect a light beam emitted by the light source;
  an eyepiece situated on the substrate, adapted to collect an incident light beam to focus it on the detector;
  reflective surfaces known as return surfaces, situated facing said substrate; and
  at least one relay lens, arranged on a reflective surface known as intermediate surface formed on the substrate, and comprising at least one field lens adapted to deviate the rays of the light beam emitted by the light source, to bring them closer to the optical axis of the eyepiece.

According to the invention, the objective, the eyepiece, the relay lens, the intermediate reflective surface, and the return reflective surfaces together form an optical system laid out such that the light beam emitted by the light source propagates by successive reflections from the objective to the eyepiece while passing through the relay lens.

The substrate is advantageously a substrate made of semi-conductor material transparent to an emission wavelength of the light source.

In a variant, the substrate is made of metal.

Preferably, the light source and the detector are arranged on a first face of the substrate, opposite to a second face of the substrate on which are arranged the objective, the eyepiece, and the relay lens.

The field lens may be a flat concave lens, a flat face of the field lens being arranged on the intermediate reflective surface and in an intermediate focus of the optical system.

The relay lens preferably comprises at least one intermediate lens intercalated between two field lenses, such that the light beam emitted by the light source propagates by successive reflections from the objective to the eyepiece while passing through the field lenses and the intermediate lens.

At least one optical element among the relay lens, the objective, and the eyepiece, may be made of high density polyethylene.

At least one optical element among the relay lens, the objective, and the eyepiece, may be constituted of a sub-wavelength lens.

Preferably, the gas sensor according to the invention is such that:
  the light source comprises a plurality of elementary sources;

the objective comprises a plurality of elementary objectives, each adapted to collect a light beam emitted by an elementary source;

the eyepiece comprises a plurality of elementary eyepieces each adapted to collect an incident light beam to focus it on the detector; and the relay lens comprises a plurality of elementary relay lenses.

The light source may comprise a plurality of elementary sources aligned on a same straight line.

In a variant, the light source may comprise a plurality of elementary sources spread out on either side of the detector and aligned along two parallel straight lines.

According to another variant, the light source comprises a plurality of elementary sources spread out on a circle centred on the detector.

At least one of the return reflective surfaces is advantageously inclined relative to the plane of the detector, such that the light beams emitted by the elementary sources are focused on a same point on the detector.

The gas sensor according to the invention may comprise a gas pre-concentrator arranged on a return reflective surface.

The gas sensor according to the invention advantageously comprises a lid receiving the return reflective surface and the gas pre-concentrator, the lid being made removable relative to the substrate.

Preferably, the light source is produced according to MEMS technology. It is for example a micro-electronic infrared source, comprising a resistive membrane forming a thermal emitter.

The detector is advantageously produced according to MEMS technology. It is for example a micro-electronic bolometer, comprising an absorbent membrane forming a thermal absorbent.

The invention also relates to an ethylometer comprising a gas sensor according to the invention, adapted to receiving a gas exhaled by a user.

BRIEF DESCRIPTION OF THE DRAWINGS

The present invention will be better understood on reading the description of examples of embodiment given for purely indicative purposes and in no way limiting, while referring to the appended drawings in which.

DETAILED DESCRIPTION OF PARTICULAR EMBODIMENTS

Figure 2:
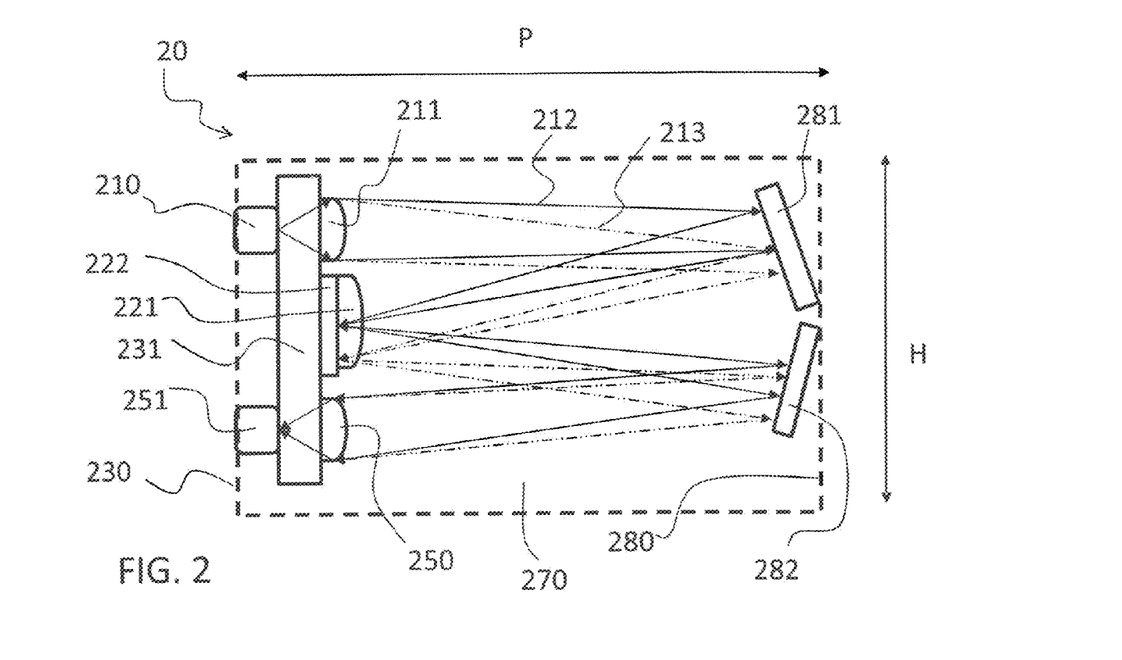
FIG. 2 illustrates a first embodiment of a gas sensor according to the invention.

A first embodiment of a gas sensor 20 according to the invention will firstly be described, with reference to FIG. 2.

The gas sensor 20 according to the invention comprises a cavity 270, for receiving a predetermined gas. This gas may be carbon dioxide, carbon monoxide, a gas for domestic usage such as methane, ethane, propane, butane, ammonia. The gas sensor may also be used for the measurement of ethanol, in an ethylometer.

A light source 210 emits a light beam in the infrared. A detector 251 receives this light beam after a course in the cavity 270 during which the light beam is partially absorbed by the gas present inside the cavity 270.

The cavity comprises two opposite interior faces 230 and 280. The cavity typically has a cylinder or rectangular parallelepiped shape, in which the faces 230 and 280 form the two bases.

On the side of the inner face 230 is located a substrate 231, for example made of semi-conductor material. The substrate 231 is for example derived from a silicon wafer having a thickness of 725 µm. It is transparent to the absorption wavelength of the gas to be detected.

On this substrate 231 are arranged the following optical elements (they are refractive optics):
  an objective 211, adapted to collect a light beam emitted by the light source 210;
  an eyepiece 250, adapted to focus an incident beam on the detector 251; and
  a relay lens 221.

The light source 210 and the detector 251 are situated on the side of the substrate opposite to the refractive optics.

The relay lens is arranged on an intermediate reflective surface 222. This intermediate reflective surface is situated advantageously between the substrate 231 and the relay lens 221.

On the side of the inner face 280 are located return reflective surfaces 281, 282. They are for example flat mirrors.

Thus, a light beam:
  is emitted by the light source 210;
  crosses the objective 211;
  crosses the cavity 270 a first time;
  is reflected on the return reflective surface 281;
  crosses the cavity 270 a second time;
  crosses the relay lens 221;
  is reflected on the intermediate reflective surface 222;
  crosses the relay lens 221 a second time;
  crosses the cavity 270 a third time;
  is reflected on the return reflective surface 282;
  crosses the cavity 270 a fourth time;
  crosses the eyepiece 250 which focuses it on the detector 251.

In other words, the objective 211, the return reflective surfaces 281, 282, the relay lens 221, the intermediate reflective surface 222 and the eyepiece 250 form together an optical system laid out so that the light beam emitted by the light source propagates by successive reflections from the objective 211 to the eyepiece 250 while passing through the relay lens 221.

The objective 211, the relay lens 221 and the eyepiece 250 together form a lens endoscope, folded back thanks to the return and intermediate reflective surfaces. In the example of FIG. 1, the relay lens is a flat-concave converging lens crossed two times: it is thus equivalent to a biconcave lens. The intermediate reflective surface 222 is situated on the flat side of the relay lens 221.

The relay lens 221 is more particularly a field lens. It is situated in an intermediate focus of the optical system as defined above. In particular, the flat face of the relay lens is situated in an intermediate focus of said optical system. This configuration is thus equivalent to a field lens in a lens endoscope, at the centre of which is situated an intermediate focus of the endoscope. The field lens 221 makes it possible to bring light rays situated at the edge of the field towards the optical axis of the eyepiece. In FIG. 2 is represented a beam 212 centred on the optical axis of the eyepiece (merged with the optical axis of the objective and the relay lens), and a beam 213 moving away from this optical axis. The beam 212 is represented in solid line, whereas the beam 213 is represented in dash and dot line. The beam 212 is focused on the flat face of the field lens 221, at the centre of this face. The beam 213 is focused at the periphery of this flat face. After crossing this field lens, the beam 212 is not deviated from the optical axis of the eyepiece, because it passes through the centre of the biconcave lens equivalent to the field lens. The beam 213, on the contrary, is deviated in the direction of the optical axis of the eyepiece, such that the beams 212 and 213 are focused by the eyepiece 250 on a same point of the detector 251. The field lens allows that the total width of the light beam propagating from the light source up to the detector remains limited. Refractive optics may thus be used, in particular an eyepiece, which have reduced diameter.

It may thus be seen that it is thereby possible to produce a gas sensor having reduced dimensions while offering a considerable length of optical path inside the cavity.

The field sensor has a reduced depth P, thanks to the return and intermediate reflective surfaces which fold back the optical path of the light beam emitted by the light source 210. The gas sensor has a reduced height H, thanks to the field lens 221 which limits the spatial broadening of the light beam during its propagation. Similarly, the width (not represented) of the field sensor remains limited thanks to the field lens 221 which limits the spatial broadening of the light beam during its propagation.

Moreover, the alignment constraints are less severe than if the light source and the detector had to be placed at the focuses of an ellipse.

It will further be noted that all of the refractive optics (objective, eyepiece, relay lens) are produced on a same surface, in particular on a same substrate. The source and the detector are situated on the side of this substrate opposite to the refractive optics. The production of a gas sensor according to the invention is thus simplified since all of the useful elements of the sensor are situated on the substrate. It is even possible to envisage producing several gas sensors according to the invention from a same substrate wafer, then to cut up the waver after fixation of the sources, detectors and refractive optics.

The focal lengths of the objective, the eyepiece and the relay lens, as well as the distances between these refractive optics, will be chosen by those skilled in the art as a function of the desired dimensions of the gas sensor. It is possible for example to adapt known optical systems forming a lens endoscope. To do so, mirrors are intercalated between the lenses of the endoscope, and the characteristics of the lenses are adjusted to take into account the double crossing of the relay lens in a gas sensor according to the invention. For example, a biconcave relay lens of radius R1-R1 belonging to a lens endoscope will be equivalent, in the optical system according to the invention, to a flat-concave lens of radius R1.

On the same model as the lens endoscopes, as many relay lenses as necessary may be provided, especially as a function of a desired depth P of the cavity 270 and of a desired length of optical path for the light beam propagating from the light source 210 up to the detector 251. As illustrated with reference to FIGS. 3A and 3B, not all of the intermediate lenses are field lenses.

For example, it is wished to obtain an optical path length of 8 cm, to measure a concentration of carbon dioxide. It is wished to obtain a depth P of the cavity equal to 1 cm, i.e. four return trips inside the cavity.

Figure 3A:
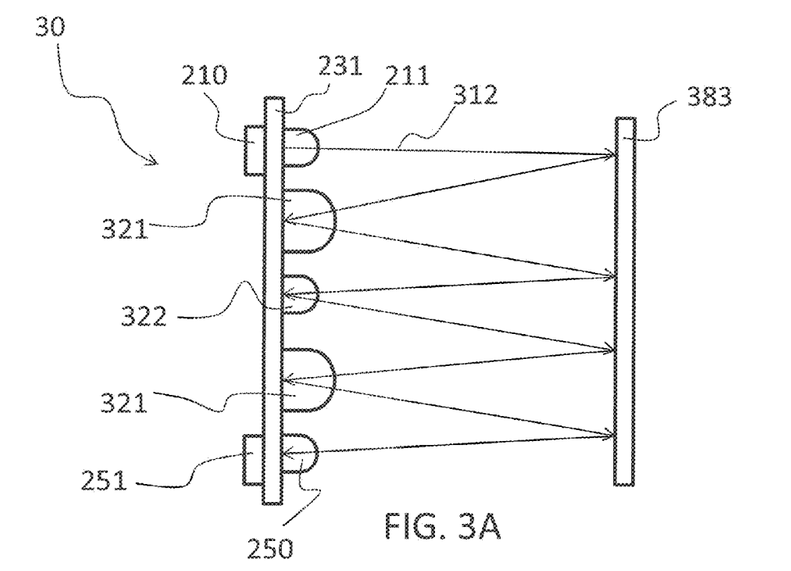
FIG. 3A schematically illustrates a second embodiment of a gas sensor according to the invention.

In FIG. 3A is represented, schematically, a second embodiment of a gas sensor 30 according to the invention. In this embodiment of the gas sensor 30 according to the invention, the light beam 312 makes four return trips inside the cavity, between the substrate 231 and a face 383 receiving the return reflective surfaces.

The light beam 312 crosses successively the objective 211, a first relay lens 321 formed of a field lens as described above, a second relay lens 322, a third relay lens 321 formed of a field lens, and the eyepiece 250. All the relay lenses are situated on an intermediate reflective surface (not represented).

The second relay lens 322 is an intermediate lens, intercalated between two field lenses.

Figure 3B:
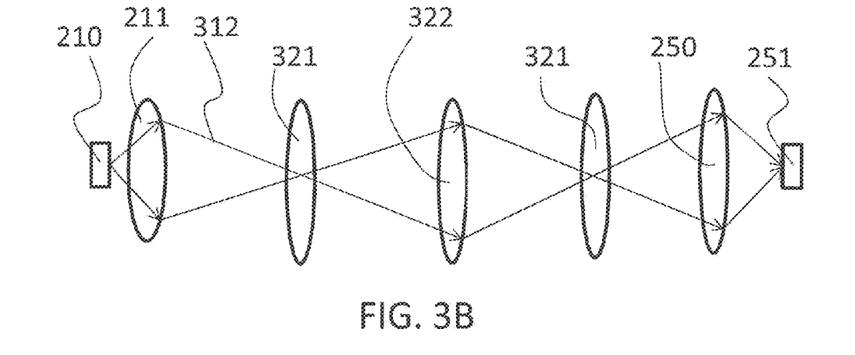
FIG. 3B schematically illustrates the "unfolded" equivalent of the gas sensor of FIG. 3A.

In FIG. 3B is represented the "unfolded" equivalent of the optical system of FIG. 3A. It is well recognised that the field lenses 321 are each situated in an intermediate focus of the optical system. Between these two field lenses is located the intermediate lens 322 which contributes to positioning the intermediate focuses on the field lenses.

FIGS. 4A to 4D schematically illustrate several variants of a third embodiment of a gas sensor according to the invention. FIGS. 4A to 4D correspond to front views of the substrate 231 receiving the refractive optics.

FIGS. 4A to 4D correspond to a gas sensor comprising an objective, a first field lens, an intermediate lens, a second field lens, and an eyepiece.

In the third embodiment of gas sensor according to the invention, the light source is produced by means of technologies derived from micro-electronics. Such a light source generally offers reduced optical power, which is why a plurality of elementary sources is advantageously used to form the light source of the gas sensor. The elementary sources are situated in a same plane. By thus increasing the emission surface of a light beam, a desired optical power is obtained.

Figure 4A:
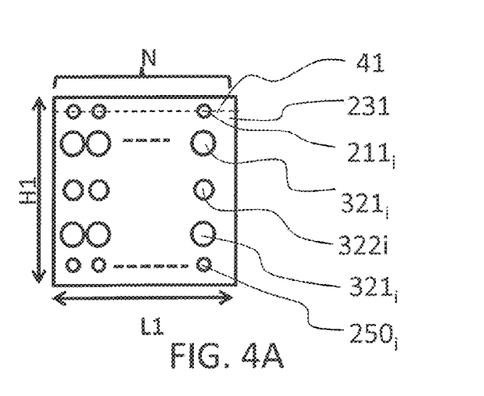
FIGS. 4A to 4D schematically illustrate several variants of a third embodiment of a gas sensor according to the invention.

In a first variant of the third embodiment of a gas sensor according to the invention, the objective, the eyepiece, and the relay lenses (field lenses and intermediate lens) are also broken down into elementary lenses. A plurality of elementary optical systems is thereby produced, each associated with an elementary source. This first variant is illustrated in FIG. 4A. The light source (not represented) is constituted of a plurality of elementary sources aligned along a same straight line 41. Each elementary optical system comprises an elementary objective $211_i$, a first elementary field lens $321_i$, an elementary intermediate lens $322_i$, a second elementary field lens $321_i$ and an elementary eyepiece $250_i$. N elementary optical systems spread out on a substrate 231 of height H1 and of width L1 are counted. For example, the substrate has a height H1 of 12 mm, a width L1 of 12 mm, and receives 10 elementary optical systems. The detector may have a bar shape.

Figure 4B:
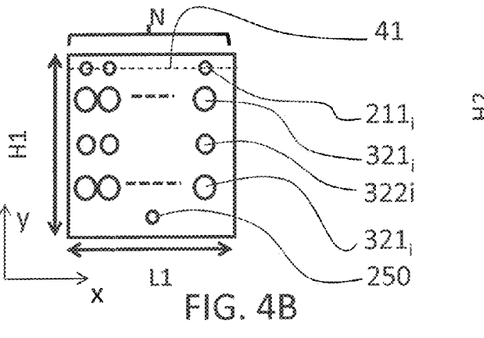

FIG. 4B illustrates a second variant of the third embodiment of a gas sensor according to the invention. FIG. 4B will only be described for its differences relative to FIG. 4A. The plane of the substrate 231 is defined by the orthogonal axes x and y. In FIG. 4B, the elementary optical systems share a single eyepiece 250. Such a characteristic is made possible by the inclination of the return reflective surfaces (not represented in FIGS. 4A to 4D). In particular, an elementary light beam emitted by an elementary source is reflected, between the second field lens $321_i$ and the eyepiece 250, on a dedicated reflective surface. For each elementary light beam (except a potential elementary light beam naturally directed on the eyepiece 250), said dedicated reflective surface is inclined around the y axis so as to deviate the elementary light beam along the x axis, in the direction of the eyepiece 250. It may be noted that said dedicated reflective surface may also be inclined around the x axis, in order to deviate the elementary light beam along the y axis, in the direction of the eyepiece 250.

It may be seen that the different elementary beams emitted by each of the elementary sources travel along different optical paths. It could be provided to take into account this factor for the calculation of the gas concentration. For example, an average length of optical path could be determined.

Those skilled in the art will easily know how to provide other variants according to this model, without going beyond the scope of the present invention. For example, it could be provided to deviate progressively the light beams towards a single eyepiece, as they propagate. To do so, an inclination will also be used around the y axis, of return reflective surfaces. The number of elementary relay lenses could thus be decreasing, considered in the order according to which they are crossed by the elementary light beams. It could also be envisaged to focus the elementary light beams on several eyepieces, less numerous than the elementary sources.

An advantage of these variants is that they make it possible to use a detector of reduced surface area, thus having a good signal to noise ratio.

Figure 4C:
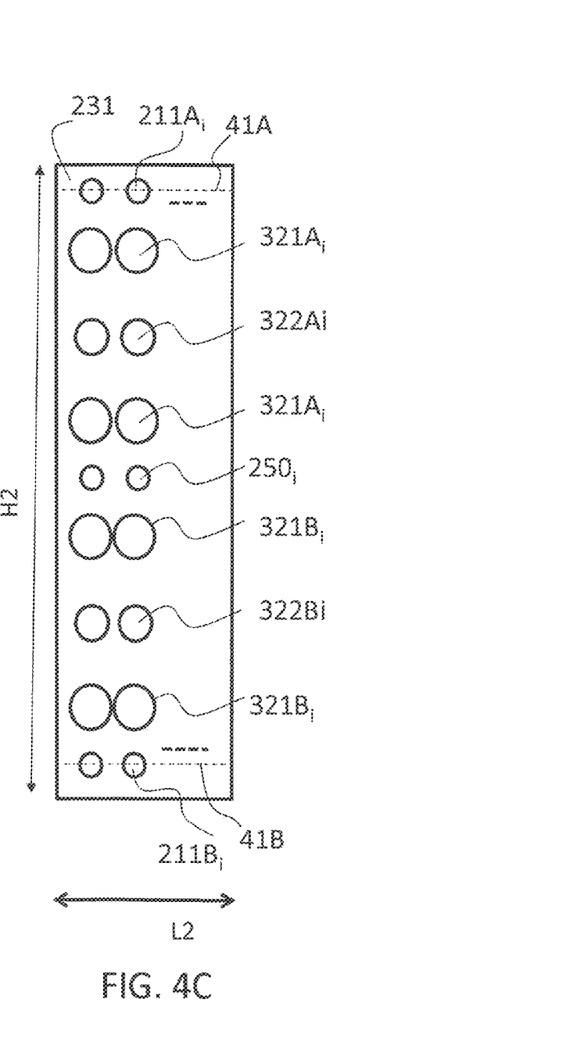

FIG. 4C illustrates a third variant of the third embodiment of a gas sensor according to the invention. FIG. 4C will only be described for its differences relative to FIG. 4A. In the embodiment of FIG. 4C, the elementary sources are aligned along two straight lines. A first group of elementary objectives $211A_i$ is aligned along one straight line 41A. A second group of elementary objectives $211B_i$ is aligned along one straight line 41B. The straight lines 41A and 41B are parallel to each other and situated on either side of the detector situated at the level of a row of elementary eyepieces $250_i$. On one side of this row of elementary eyepieces $250_i$ are located successive rows of first elementary field lenses $321A_i$, elementary intermediate lenses $322A_i$, and second elementary field lenses $321A_i$. The configuration of FIG. 4A is observed. On the other side of the row of elementary eyepieces $250_i$ are located other successive rows of first elementary field lenses $321B_i$, elementary intermediate lenses $322B_i$, and second elementary field lenses $321B_i$. It may thus be seen that for a same number of elementary sources, this variant makes it possible to spread out the bulk of the refractive optics on the substrate in the sense of its height H2, and not uniquely in the sense of its width L2.

Figure 4D:
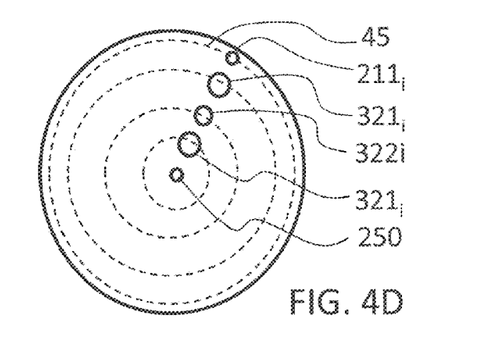

FIG. 4D illustrates a fourth variant corresponding to elementary sources spread out along a circle 45 centred on a detector point. The elementary objectives $211_i$, and elementary relay lenses $321_i$, $322_i$ are spread out in concentric circles around a single eyepiece 250. It is thus possible to use a detector of reduced surface area, having a good signal to noise ratio.

Numerous additional variants of distribution of the elementary sources relative to the detector could be envisaged, without going beyond the scope of the present invention. For example, the distribution of the optical elements on the substrate will depend on the distribution of the elementary sources relative to the detector.

Numerous variants implementing a light source or a plurality of elementary light sources, and a detector or a plurality of elementary detectors, could also be envisaged without going beyond the scope of the present invention.

Figure 5:
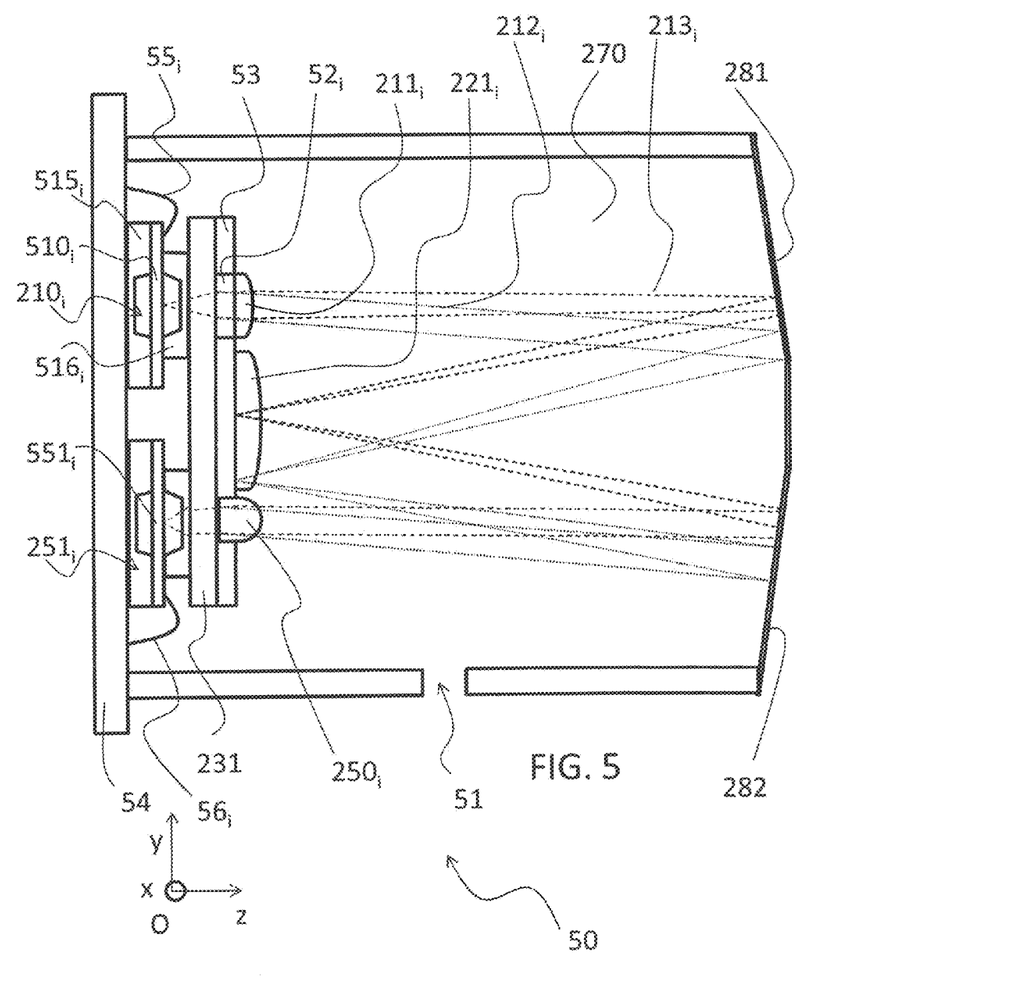
FIG. 5 illustrates a fourth embodiment of a gas sensor according to the invention.

FIG. 5 illustrates a fourth embodiment of gas sensor 50 according to the invention. FIG. 5 will only be described for its differences relative to FIG. 2.

In FIG. 5 is represented an opening 51, for the input of the gas to be detected inside the cavity 270. This opening here has a disc shape of 1 cm diameter. In a variant, the gas enters via a plurality of smaller openings, or via at least two openings situated face to face, on either side of the cavity 270.

The light source is constituted of a plurality of elementary light sources $210_i$ each associated with an elementary objective $211_i$, an elementary relay lens $221_i$ and an elementary eyepiece $250_i$. In a similar manner to the embodiment of FIG. 4A, the elementary light sources are aligned together. The gas sensor 50 is represented along a sectional view in the plane (yOz), orthogonal to a straight line on which are aligned the elementary light sources. In FIG. 5 is represented the elementary beams $212_i$ and $213_i$ corresponding respectively to the beams 212 and 213 of FIG. 2.

The mirror 281 is a flat mirror inclined at an angle of −3.5° around the x axis (axis orthogonal to the plane (yOx)). The mirror 282 is a flat mirror inclined at an angle of +3.5° around the x axis. In a variant in which the gas sensor could comprise more than one relay lens, for example three, it could be provided that the other return reflective surfaces are flat and parallel to the plane (xOy). Separate flat mirrors for each elementary optical system could be provided.

Between the elementary source $210_i$ and the objective $211_i$ is located an elementary optical filter $52_i$ as explained above, intended to select a range of useful wavelengths for a measurement of the concentration of a predetermined gas.

In the example represented in FIG. 5, the elementary optical filter $52_i$ is formed on the substrate 231. In FIG. 5, the elementary optical filter $52_i$ is superposed on the elementary objective $211_i$. In a variant, it may be superposed on the elementary eyepiece $250_i$ or superposed on the elementary relay lens $221_i$, or a combination of these several possibilities. The substrate 231 is thus functionalised to the utmost, which facilitates the manufacture of the gas sensor according to the invention. The transfer function of the filter (high pass, low pass, band pass) will be different as a function of its positioning.

The substrate 231 is covered with a layer of reflective material 53, except opposite the elementary light sources $210_i$ and the elementary detectors $251_i$. This layer of reflective material 53 forms an intermediate reflective surface as defined with reference to FIG. 2. It also makes it possible to prevent the arrival of parasitic light on the detector.

The main steps of producing a gas sensor as represented in FIG. 5 will now be described.

The substrate 231 for example made of semi-conductor material is derived from a silicon wafer, of 725 μm thickness. It is thus transparent to the wavelengths of interest.

On this substrate is deposited a layer of reflective material, for example a metal such as gold or aluminium. Other materials such as silver or copper could also be envisaged.

Holes of around 1 mm diameter are etched in the layer of reflective material, so as to make cut outs in the layer of reflective material 53 opposite the elementary light sources $210_i$ and the elementary detectors $251_i$. This etching is carried out preferably following a step of photolithography which makes it possible to define the zones where to make the openings of the reflective material. The actual etching will be able to be wet or dry depending on the material. Photolithography comprises for example steps of depositing a photosensitive resin, superposition of a mask and etching of the resin by means of exposure to ultraviolet radiation. The actual etching is for example a chemical attack of the layer 53 through the etched resin.

A substrate 231 covered with a layer of reflective material 53 with cut outs is obtained.

In a variant, the substrate 231 is a material not transparent to the wavelengths of interest, and cut out opposite the light source and the detector. It is for example a metal. This metal may be reflective, such that the intermediate reflective surface receiving the relay lens according to the invention is formed by one face of the substrate.

On the layer of reflective material 53 with cut outs is carried out a deposition intended to form the elementary optical filters $52_i$. The elementary optical filter $52_i$ may be formed of a metal-dielectric multilayer stack or of a high index-low index multilayer stack. For example, an elementary optical filter $52_i$ is formed of a metal-dielectric stack of 5 layers, or of a high index-low index dielectric stack of 12 layers. The deposit is then etched. It is only conserved in the openings of the layer made of reflective material 53 intended to be placed opposite an elementary source. In a variant, it is only conserved in the openings of the layer made of reflective material 53 intended to be placed opposite an elementary detector or an elementary relay lens, or in several of these types of opening (see above).

The elementary objectives $211_i$, elementary relay lenses $221_i$ and elementary eyepieces $250_i$ are then formed.

Advantageously, these different refractive optics are formed in the following manner:
- a nickel mould known as "master" is etched, according to the complementary shape of a desired shape for an optic;
- a useful material is poured into the mould. The useful material is for example HDPE (high density polyethylene). Whatever the case it will be a material sufficiently transparent in the target spectral range, and which can be printed. Its glass transition temperature Tg must be such that on heating it, it can be softened sufficiently to then be able to give it the desired shape;
- the useful material such as HDPE is heated, so that it softens and so that it takes the shape of the mould;
- after the useful material has cooled, the mould is placed in the desired spot, against the layer made of reflective material 53, or against an elementary optical filter. The useful material adheres to the layer made of reflective material 53 or to the elementary optical filter, and forms an elementary objective $211_i$, an elementary relay lens $221_i$ or an elementary eyepiece $250_i$.

Advantageously, the set of elementary objectives $211_i$, elementary relay lenses $221_i$ and elementary eyepieces $250_i$ is formed at the same time, by means of a single nickel wafer. Thus, the different refractive optics are formed at the same time, according to a collective manufacturing method.

An advantage of the invention is thus that manufacture may be carried out at low cost and on a large scale.

For example, the elementary objective $211_i$ is an aspherical lens of 700 μm diameter and of 200 μm height, and the elementary eyepiece $250_i$ is an aspherical lens of 2 mm diameter. The relay lens has a diameter at the most equal to 2 mm. The aspherical shape of the optics makes it possible to conserve a dense light beam. The objective and the eyepiece must be very open optics, to collect a maximum of luminous flux.

Each elementary source $210_i$ is advantageously an elementary infrared source based on a micro-electromechanical (or MEMS, for "Microelectromechanical system") type technology. The elementary source $210_i$ comprises a resistive membrane $510_i$ forming a heat emitter. This membrane is called resistive because it is covered with metal tracks, arranged according to concentric circles. By supplying a current to the resistive membrane $510_i$, it heats up and forms an infrared radiation source. The resistive membrane $510_i$ is suspended above a silicon crucible $515_i$, and protected by a cap $516_i$ transparent to infrared wavelengths. The cap may be formed of a sample of silicon substrate of 725 μm thickness, having a hollow of 300 μm depth. The cavity formed between the crucible $515_i$ and the cap $516_i$ may have particular pressure conditions. For example, a partial vacuum is formed between the crucible $515_i$ and the cap $516_i$. The resistive membrane $510_i$ is for example a membrane of silicon nitride ($Si_3N_4$) of 100 nm thickness and of 150 μm diameter. Those skilled in the art will easily know how to find in the literature all the details necessary to produce such an elementary source. The term "micro-hotplate IR-source" is usually used to designate such a source. The term "micro-filament" may also be used.

In the same way, each elementary detector $251_i$ is advantageously an infrared bolometer based on an MEMS type technology. The elementary detector $251_i$ comprises a heat absorbing membrane $551_i$. An incident infrared radiation on the membrane $551_i$ heats the latter. The heat absorbed by the membrane $551_i$ is converted into an electrical signal, which makes it possible to quantify the light intensity of the incident infrared radiation. The membrane $551_i$ is for example a membrane made of vanadium oxide having a square surface of 28 μm sides and a thickness of 1 μm. It may be surmounted by a precise stack of additional layers, for example a stack of Si (300 nm), YSZ (40 nm), $CeO_2$ (10 nm), GBCO (50 nm) and $PtO_x$ (200 nm). Those skilled in the art will easily know how to find in the literature all the details necessary to produce such an elementary detector. In a variant, each elementary detector $251_i$ may be a thermopile or a pyrometer, also produced according to MEMS technology.

The elementary sources $210_i$ and the elementary detectors $251_i$ are then deposited and bonded in a same plane, on the substrate 231, and on the side opposite to the refractive optics. The deposition implements a known technique called "pick and place". The assembly is then bonded onto a printed circuit wafer 54. The printed circuit wafer 54 is especially a PCB (Printed Board Circuit), and more particularly an ASIC (Application-Specific Integrated Circuit). Each elementary source $210_i$ is electrically supplied by a connecting wire $55_i$, and each elementary detector $251_i$ is connected to the printed circuit 54 by a connecting wire $56_i$. The wiring by means of connecting wires $55_i$ and $56_i$ may be formed by a technique known as "wire bonding". In particular, the wiring may be formed by a connection known as "ball bonding". Alternatively, the wiring may be formed by a connection known as TSV (Through Silicon Vias).

A case, open on one of its faces, is then bonded onto the printed circuit 54 to form, between the inside of this case and the printed circuit 54, the cavity 270 of the gas sensor according to the invention. The return reflective surfaces are formed inside the case. The return reflective surfaces are flat mirrors, which is why the bonding of the case does not require precise alignment. Different variants could be envisaged to form the return reflective surfaces, without going beyond the scope of the present invention. For example, the bottom of the case may receive a single flat mirror, or several separate mirrors potentially inclined differently to each other, or a single mirror structured so as to form several reflective surfaces inclined differently to each other.

Figure 6:
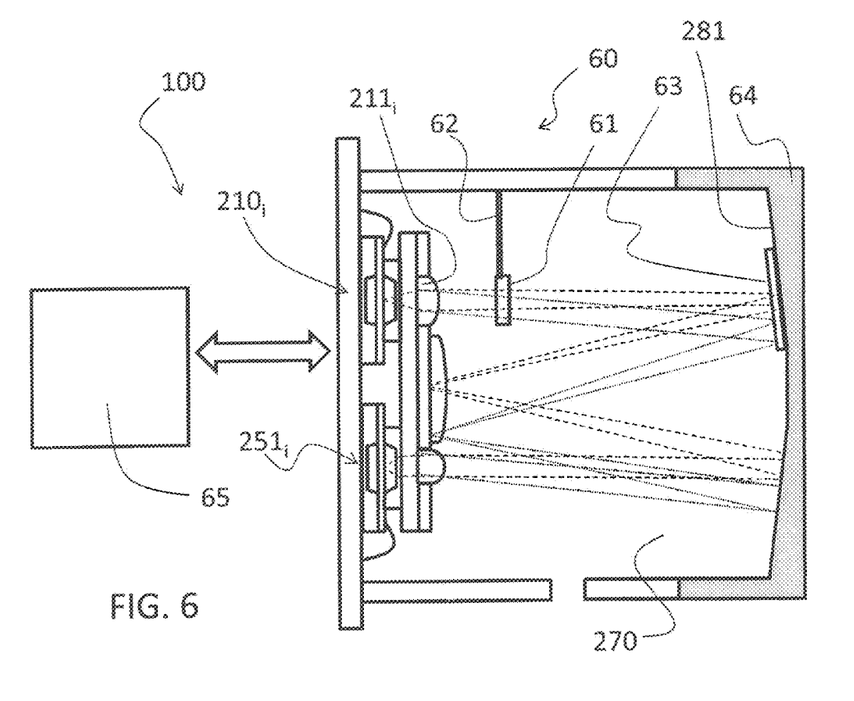
FIG. 6 illustrates a sixth embodiment of gas sensor according to the invention.

FIG. 6 illustrates a sixth embodiment of gas sensor 60 according to the invention.

The gas sensor 60 will only be described for its differences relative to the gas sensor 50 of FIG. 5.

The gas sensor 60 comprises an optical filter 61 arranged on the optical path of the light beam, at the output of the elementary objective $211_j$. It replaces the elementary optical filters $52_i$ as described with reference to FIG. 5. An advantage is that the optical filter 61 is then arranged at the spot where the light beam is in quasi-normal incidence, which enhances its efficiency.

The optical filter 61 has for example a surface area of $2 \times 10$ mm$^2$: it extends at the outlet of the set of elementary objectives $211_j$. The optical filter 61 is maintained by a support 62. In a variant, it may be envisaged to place the optical filter 61 on a return reflective surface or under a relay lens. The alignment of the optical filter relative to the other elements of the gas sensor 60 does not need to be precise, which is why it may be done by hand.

The gas sensor 60 further comprises a gas pre-concentrator 63, also called "gas absorber". A pre-concentrator is a device which is going to concentrate therein a large quantity of the gas present in the cavity 270. Thus, by placing a pre-concentrator in the optical path of the light beam inside the cavity 270, it is assured that said light beam intersects with a maximum number of molecules of said gas present in the cavity. The light beam inside the cavity crosses the pre-concentrator 63, is reflected on the return reflective surface 281, then again crosses the pre-concentrator 63. The absorption by the gas is thus maximal. In other words, a pre-concentrator makes it possible that the gas to be measured is more present on the optical path of the light beam inside the cavity 270. Thus, it is possible to detect the presence of a gas, and to determine its concentration in the cavity, for a reduced length of optical path. The gas sensor 60 thereby formed is also adapted to measure low concentrations of a gas, or to carry out measurements on a gas having a low absorption cross-section.

In the example represented in FIG. 6, the gas sensor 60 forms part of an ethylometer 100, but numerous other devices being able to include such a gas sensor could be envisaged, for example sensors of volatile organic compounds such as formaldehyde. The pre-concentrator 63 of FIG. 6 thus makes it possible to concentrate ethanol, but pre-concentrators to concentrate formaldehyde or another volatile organic compound could be envisaged.

The pre-concentrator 63 is placed on one of the return reflective surfaces. According to a variant, not represented, each return reflective surface is covered by the pre-concentrator or by a dedicated pre-concentrator. In the example represented in FIG. 6, the pre-concentrator 63 is placed on the return reflective surface 281.

A drawback of a pre-concentrator is that it does not release the gas once the latter has been absorbed. Thus it may be seen that it is necessary to replace the pre-concentrator after each measurement carried out by means of the gas sensor 60.

The gas sensor 60 has a removable lid 64, receiving the return reflective surfaces and the pre-concentrator 63. Thus, after each use of the ethylometer 100, the pre-concentrator 63 may be easily replaced. As set out above, the return reflective surfaces do not require a precise alignment relative to the other elements of the gas sensor 60. It may thus be envisaged to remove and replace the removable lid 64, by hand, without deteriorating the performances of the gas sensor 60. A compact, precise and inexpensive gas sensor is thereby produced.

The gas sensor 60 is connected to a measuring and supply module 65. The measuring and supply module especially comprises calculation means for measuring a concentration of ethanol in the air in the cavity 270, implementing a calculation of a ratio between the light intensity received by the detector and the light intensity emitted by the light source.

The measurement and supply module 65 may comprise electronic means and computer and/or software means. It is typically a digital or analogue electronic circuit, preferably dedicated, associated with a microprocessor and/or a computer.

Figure 7:
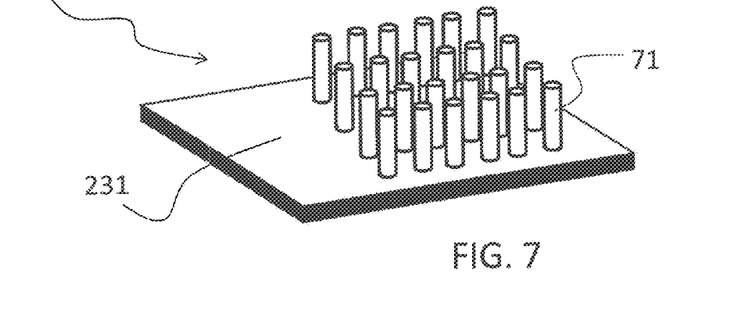
FIG. 7 illustrates an array which can be a sub-wavelength lens used in a gas sensor according to the invention.

In FIG. 7 is represented an array forming a sub-wavelength lens 70, which may be used as objective, eyepiece and/or relay lens, in a gas sensor according to the invention. In other words, at least one of these refractive optics may be formed of a sub-wavelength lens 70, also known as sub-wavelength array, or sub-lambda lens.

The sub-wavelength lens 70 is formed of nanostructures of nanometric dimensions, for example studs 71. The studs may be arranged in a square matrix, a honeycomb, these two examples not being limiting. In a variant, these nanostructures may be holes, rays, or any other pattern. They may also be a concentric circle in which the step is less than the wavelength and the centre of which corresponds to the optical axis of the sub-wavelength lens 70. This optical axis is then advantageously merged with the optical axis of the light source (or of an elementary light source), corresponding to the optical axis of the detector (or of a corresponding elementary detector).

The characteristic dimension of these nanostructures is much less than the wavelength of the light beam emitted by the light source. For example, these nanostructures are studs of which the section is much less than said wavelength.

For example, the incident light beam has a wavelength comprised between 2 μm and 10 μm, and the cross section of a stud is of the order of 400 nm. The height of a stud is comprised between 4 μm and 10 μm. The density of the studs varies between the centre of the sub-wavelength lens and the edges of the sub-wavelength lens. Thus, at the scale of the wavelength of the incident light beam, the sub-wavelength lens 70 has a graded index and acts as a refractive optic.

The sub-wavelength lens 70 is advantageously etched in a silicon layer. Preferably, a pre-existing silicon layer of the gas sensor is used, to etch therein a sub-wavelength lens forming a refractive optic.

According to a first variant, the sub-wavelength lens 70 is etched on the face of the silicon substrate 231 opposite to the face receiving the source and the detector. Preferably, only the objective and the eyepiece are formed of a sub-wavelength lens.

Figure 8A:
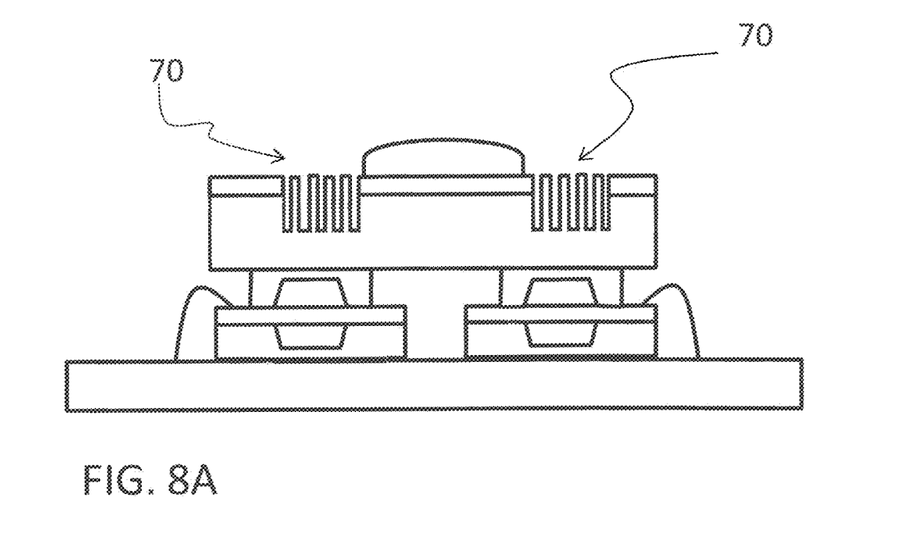
FIGS. 8A and 8B illustrated a detailed view of a gas sensor according to the invention in which at least one refractive optic is formed of a sub-wavelength lens.

FIG. 8A illustrates an example of this first variant. FIG. 8A represents a detail of FIG. 6, and differs from FIG. 6 in that the elementary objectives and elementary eyepieces are each formed of a sub-wavelength lens 70 etched on the face of the silicon substrate opposite to the face receiving the source and the detector.

Figure 8B:
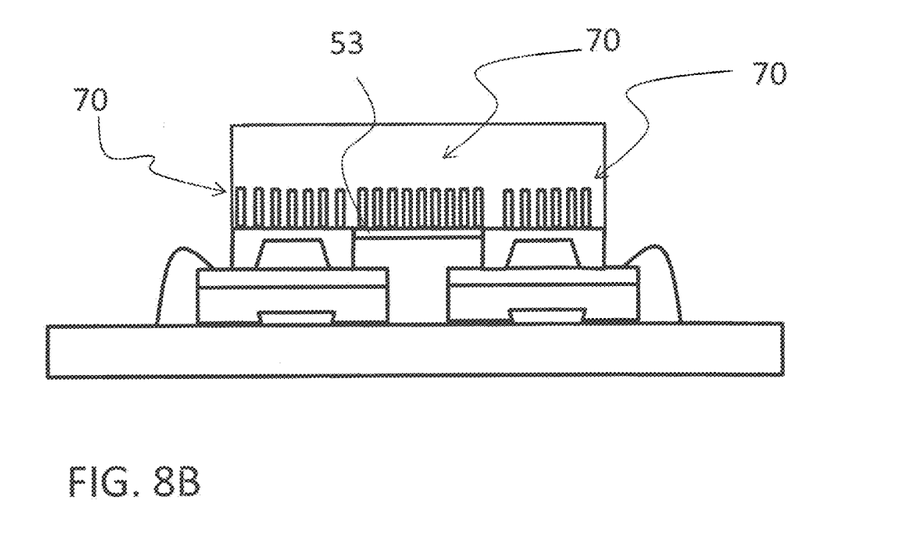

According to a second variant, the sub-wavelength lens 70 is etched on the face of the silicon substrate receiving the source and the detector. FIG. 8B illustrates an example of this second variant. In the example represented in FIG. 8B, the objective, the eyepiece and the relay lens are formed of a sub-wavelength lens. FIG. 8B represents a detail of FIG. 6, and differs from FIG. 6 in that the elementary objectives, elementary eyepieces and elementary relay lenses are each formed of a sub-wavelength lens 70 etched on the face of the silicon substrate receiving the source and the detector. The layer made of reflective material 53 is located under the relay lens, thus this time on the side of the substrate receiving the source and the detector.

According to a third variant, the sub-wavelength lens 70 is etched on a lower or upper face of the cap protecting the light source or the detector (see description with reference to FIG. 5).

An advantage of such a sub-wavelength lens 70 is that it makes it possible to further reduce the size of a gas sensor according to the invention, since at least some of the refractive optics form an integral part of the silicon substrate or of a silicon cap belonging to the source or to the detector.

The invention is not limited to the examples that have just been described, and numerous variants could be envisaged without going beyond the scope of the present invention. In particular, other examples of sources or detectors could be implemented, especially sources and detectors adapted to be mounted on a substrate and according to a technology known as "wafer-level packaging".

The invention claimed is:

1. Gas sensor (20; 30; 50; 60) comprising a cavity (270) for receiving a gas, a light source (210) and a detector (251), characterised by:
   a substrate (231);
   an objective (211) situated on the substrate (231), adapted to collect a light beam (212, 213) emitted by the light source (210);
   an eyepiece (250) situated on the substrate (231), adapted to collect an incident light beam to focus it on the detector (251);
   reflective surfaces known as return surfaces (281, 282), situated facing said substrate; and
   at least one relay lens (221; 321, 322), arranged on a reflective surface known as intermediate surface (222) formed on the substrate (231), and comprising at least one field lens (221; 321) adapted to deviate the rays (213) of the light beam emitted by the light source, to bring them closer to the optical axis of the eyepiece (250);
the objective (211), the eyepiece (250), the relay lens (221; 321, 322), the intermediate reflective surface (222), and the return reflective surfaces (281, 282) together forming an optical system laid out such that the light beam (212, 213) emitted by the light source (210) propagates by successive reflections from the objective (211) to the eyepiece (250) while passing through the relay lens (221; 321, 322).

2. Gas sensor (20; 30; 50; 60) according to claim 1, characterised in that the light source (210) and the detector (251) are arranged on a first face of the substrate (231), opposite a second face of the substrate (231) on which are arranged the objective (211), the eyepiece (250), and the relay lens (221; 321, 322).

3. Gas sensor (20; 30; 50; 60) according to claim 1, characterised in that the field lens (221; 321) is a flat concave lens, one flat face of the field lens being arranged on the intermediate reflective surface (222) and in an intermediate focus of the optical system.

4. Gas sensor (30) according to claim 1, characterised in that the relay lens comprises at least one intermediate lens (322) intercalated between two field lenses (322), such that the light beam (212, 213) emitted by the light source (210) propagates by successive reflections from the objective (211) to the eyepiece (250) while passing through the field lenses (321) and the intermediate lens (322).

5. Gas sensor (20; 30; 50; 60) according to claim 1, characterised in that at least one optical element among the relay lens (221; 321, 322), the objective (211), and the eyepiece (250), is constituted of a sub-wavelength lens (70).

6. Gas sensor (50; 60) according to claim 1, characterised in that:
   the light source comprises a plurality of elementary sources ($210_i$);
   the objective comprises a plurality of elementary objectives ($211_i$; $211A_i$, $211B_i$), each adapted to collect a light beam emitted by an elementary source ($210_i$);
   the eyepiece comprises a plurality of elementary eyepieces ($250_i$) each adapted to collect an incident light beam to focus it on the detector; and
   the relay lens comprises a plurality of intermediate relay lenses ($212_i$; $321_i$, $322_i$; $321A_i$, $321B_i$, $322A_i$, $322B_i$).

7. Gas sensor (50; 60) according to claim 6, characterised in that at least one of the return reflective surfaces (281, 282) is inclined relative to the plane of the detector, such that the light beams emitted by the elementary sources ($210_i$) are focused on a same point on the detector.

8. Gas sensor (50; 60) according to claim 1, characterised in that the light source comprises a plurality of elementary sources ($210_i$) aligned on a same straight line (41).

9. Gas sensor (50; 60) according to claim 1, characterised in that the light source comprises a plurality of elementary sources ($210_i$) spread out on either side of the detector and aligned along two parallel straight lines (41A, 41B).

10. Gas sensor (50; 60) according to claim 1, characterised in that the light source comprises a plurality of elementary sources ($210_i$) spread out on a circle (45) centred on the detector.

11. Gas sensor (60) according to claim 1, characterised by a gas pre-concentrator (63) arranged on a return reflective surface (281; 282).

12. Gas sensor (20; 30; 50; 60) according to claim 11, characterised in that it comprises a lid (64) receiving the return reflective surface and the gas pre-concentrator (63), the lid (64) being made removable relative to the substrate (231).

13. Gas sensor (20; 30; 50; 60) according to claim 1, characterised in that the light source (210; $210_i$) is a microelectronic infrared source, comprising a resistive membrane ($510_i$) forming a thermal emitter.

14. Gas sensor (20; 30; 50; 60) according to claim 1, characterised in that the detector (251; $251_i$) is a microelectronic bolometer, comprising an absorbent membrane ($551_i$) forming a thermal absorbent.

15. Ethylometer (100) comprising a gas sensor adapted to receive a gas exhaled by a user, characterised in that the gas sensor is a gas sensor (20; 30; 50; 60) according to claim 1.

* * * * *